(12) United States Patent
Oberholzer

(10) Patent No.: US 10,143,543 B2
(45) Date of Patent: Dec. 4, 2018

(54) APPARATUS AND METHOD FOR STORING AND DISPENSING DENTAL FLOSS

(71) Applicant: PERI-DENT LTD, London (GB)

(72) Inventor: Mark Oberholzer, Galashiels (GB)

(73) Assignee: PERI-DENT LTD, London (GB)

( * ) Notice: Subject to any disclaimer, the term of this patent is extended or adjusted under 35 U.S.C. 154(b) by 0 days.

(21) Appl. No.: 15/454,877

(22) Filed: Mar. 9, 2017

(65) Prior Publication Data
US 2018/0185126 A1    Jul. 5, 2018

(51) Int. Cl.
*A61C 15/04*   (2006.01)
*A61C 15/00*   (2006.01)

(52) U.S. Cl.
CPC ........ *A61C 15/043* (2013.01); *A61C 2202/00* (2013.01)

(58) Field of Classification Search
CPC ......... A61B 17/06; A61B 19/02; A61C 15/00; A61C 15/04; A61C 15/043; B65D 25/22; B65D 75/325
USPC ................ 132/321, 323–327; 206/63.5, 388, 206/461–471; 220/524
See application file for complete search history.

(56) References Cited

U.S. PATENT DOCUMENTS

| | | | | |
|---|---|---|---|---|
| 2,950,004 A | * | 8/1960 | Acomb | B65D 75/305 206/471 |
| 4,327,755 A | * | 5/1982 | Endelson | A61C 15/043 132/324 |
| 4,693,365 A | * | 9/1987 | Corella | A61C 15/043 206/388 |
| 4,852,728 A | * | 8/1989 | Court | A61C 15/043 132/321 |
| 4,881,560 A | * | 11/1989 | Blank | A61C 15/043 132/324 |
| 5,065,861 A | | 11/1991 | Greene et al. | |

(Continued)

FOREIGN PATENT DOCUMENTS

| CN | 205181505 U | 4/2016 |
|---|---|---|
| EP | 0080440 A1 | 6/1983 |

(Continued)

OTHER PUBLICATIONS

Intellectual Property Office , Combined Search and Examination Report for Application No. GB1622368.7, dated May 9, 2017.

*Primary Examiner* — Bryon Gehman
(74) *Attorney, Agent, or Firm* — Marshall, Gerstein & Borun LLP

(57) ABSTRACT

Examples of the present disclosure relate to an apparatus and method for storing and dispensing dental floss. In some examples, there is provided an apparatus for housing and dispensing dental floss, the apparatus comprising: a first compartment integrally formed with a second compartment; wherein the first compartment is configured, in use, to house dental floss; wherein the second compartment is configured, in use, to provide user access to a length of the stored dental floss for dispensement therefrom; wherein at least the second compartment is closed by a sealing member; and wherein at least a portion of the sealing member is configured to be detachable to provide user access to the interior of the second compartment so as to provide, in use, access to the length of the stored dental floss for dispensement.

18 Claims, 4 Drawing Sheets

(56) References Cited

U.S. PATENT DOCUMENTS

| | | | |
|---|---|---|---|
| 5,156,311 A * | 10/1992 | Spencer, Jr. | A61C 15/043 206/389 |
| 5,251,651 A | 10/1993 | Mason | |
| 5,322,077 A * | 6/1994 | Corella | A61C 15/043 132/323 |
| 5,722,439 A * | 3/1998 | Endelson | A61C 15/043 132/321 |
| 5,806,666 A | 9/1998 | Chiang et al. | |
| 6,302,121 B1 | 10/2001 | McConnell | |
| 6,488,036 B1 | 12/2002 | Francis | |
| 6,497,236 B1 | 12/2002 | Yates et al. | |
| 6,571,804 B2 | 6/2003 | Adler | |
| 6,678,239 B2 * | 1/2004 | Clemens | B65D 75/30 206/308.1 |
| 6,705,328 B1 | 3/2004 | Ramirez | |
| 6,715,603 B1 | 4/2004 | Uribe | |
| 7,213,604 B2 | 5/2007 | Romine | |
| 7,665,600 B1 | 2/2010 | Griffin | |
| 7,841,350 B2 | 11/2010 | Kernot | |
| 7,942,155 B2 | 5/2011 | Van Iderstine | |
| 8,006,708 B1 | 8/2011 | Burr, Jr. | |
| 8,100,261 B2 | 1/2012 | Longoni et al. | |
| 8,251,076 B2 | 8/2012 | Souza | |
| 8,256,439 B1 | 9/2012 | Stinson | |
| 8,348,050 B2 * | 1/2013 | Grossman | A61C 15/043 132/321 |
| 8,534,463 B2 * | 9/2013 | Smith | B65D 81/022 206/461 |
| 8,671,958 B2 | 3/2014 | Borg et al. | |
| 9,125,713 B2 * | 9/2015 | Zajas | A61C 15/04 |
| 2002/0088474 A1 | 7/2002 | Montalvo | |
| 2005/0000538 A1 | 1/2005 | Blasi et al. | |
| 2006/0196909 A1 | 9/2006 | Hadtke et al. | |
| 2007/0074991 A1 * | 4/2007 | Heisserer | A61F 2/0095 206/438 |
| 2008/0257377 A1 | 10/2008 | Burrows | |
| 2009/0101164 A1 | 4/2009 | Berg et al. | |
| 2010/0139688 A1 * | 6/2010 | Musgrave | A61C 15/043 132/321 |
| 2010/0252063 A1 | 10/2010 | Grossman | |
| 2012/0234889 A1 | 9/2012 | Kim | |
| 2013/0025623 A1 | 1/2013 | Herzog | |
| 2016/0199163 A1 | 7/2016 | Kabrin | |

FOREIGN PATENT DOCUMENTS

| | | |
|---|---|---|
| EP | 0666224 A1 | 8/1995 |
| EP | 0792123 A1 | 9/1997 |
| EP | 2670342 B1 | 10/2015 |
| JP | 2005335742 A | 12/2005 |
| JP | 2006204556 A | 8/2006 |
| KR | 20020063152 A | 8/2002 |
| KR | 200346030 Y1 | 3/2004 |
| KR | 20130084840 A | 7/2013 |
| WO | WO-93/16654 A1 | 9/1993 |
| WO | WO-9709943 A1 | 3/1997 |
| WO | WO-01/05665 A2 | 1/2001 |
| WO | WO-07017194 A1 | 2/2007 |
| WO | WO-2010/082103 A1 | 7/2010 |
| WO | WO-10082103 A1 | 7/2010 |
| WO | WO-2012/124871 A1 | 9/2012 |
| WO | WO-13015620 A2 | 1/2013 |
| WO | WO-15128686 A1 | 9/2015 |

* cited by examiner

APPARATUS AND METHOD FOR STORING AND DISPENSING DENTAL FLOSS

CROSS-REFERENCE TO RELATED APPLICATIONS

This patent application claims the priority of the United Kingdom Application No. 1622368.7, entitled Apparatus and Method for Storing and Dispensing Dental Floss, filed on Dec. 29, 2016, of which is incorporated herein by reference in its entirety.

TECHNOLOGICAL FIELD

Examples of the present disclosure relate to an apparatus and method for storing and dispensing dental floss. Some examples, though without prejudice to the foregoing, relate to a combined retail package and container/dispenser for dental floss.

BACKGROUND

Typically, a roll or bobbin of dental floss would be stored in a box or container with a hinged cap concealing the dental floss and a metal cutter fitment. Such a dental floss container would usually be packaged in a blister pack with a backing card for a retail environment. Such conventional packaging and containers for dental floss are not always optimal. It is useful to provide a dental floss package and container that may reduce the amount of materials required for manufacturing the same, whilst enabling the stored dental floss to be kept fresh.

The listing or discussion of any prior-published document or any background in this specification should not necessarily be taken as an acknowledgement that the document or background is part of the state of the art or is common general knowledge. One or more aspects/examples of the present disclosure may or may not address one or more of the background issues.

BRIEF SUMMARY

According to at least some examples of the disclosure there is provided an apparatus for housing and dispensing dental floss, the apparatus comprising:
a first compartment integrally formed with a second compartment;
wherein the first compartment is configured, in use, to house dental floss;
wherein the second compartment is configured, in use, to provide user access to a length of the stored dental floss for dispensement therefrom;
wherein at least the second compartment is closed by a sealing member; and
wherein at least a portion of the sealing member is configured to be detachable to provide user access to the interior of the second compartment so as to provide, in use, access to the length of the stored dental floss for dispensement.

According to at least some examples of the disclosure there is provided an apparatus for housing and dispensing dental floss, the apparatus comprising:
a first compartment means integrally formed with a second compartment means;
wherein the first compartment means is configured, in use, to house dental floss;
wherein the second compartment means is configured, in use, to provide user access to a length of the stored dental floss for dispensement therefrom;
wherein at least the second compartment means is closed by sealing means; and
wherein at least a portion of the sealing means is configured to be detachable to provide user access to the interior of the second compartment means so as to provide, in use, access to the length of the stored dental floss for dispensement.

According to at least some examples of the disclosure there is provided a method for manufacturing an apparatus for storing and dispensing dental floss comprising:
integrally forming first and second compartments in a body member, wherein the first compartment is configured, in use, to store dental floss, and wherein the second compartment is configured, in use, to provide user access to a length of the stored dental floss;
placing dental floss in the first compartment;
sealing the second compartment with a sealing member such that at least a portion of the sealing member is detachable to provide user access to the interior of the second compartment.

According to at least some examples of the disclosure there are provided examples as claimed in the appended claims.

BRIEF DESCRIPTION OF THE DRAWINGS

For a better understanding of various examples of the present disclosure that are useful for understanding the detailed description and certain embodiments of the invention, reference will now be made by way of example only to the accompanying drawings in which.

Figure 1A:
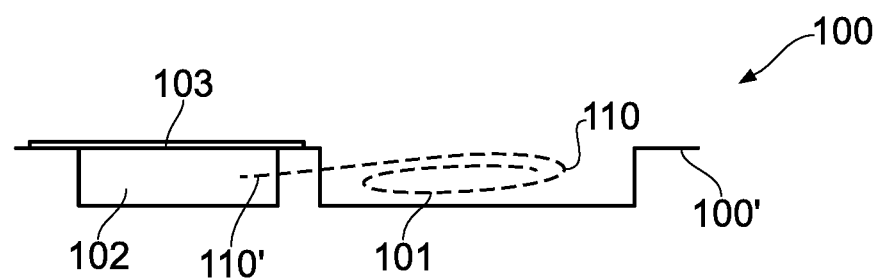
FIGS. 1A and 1B schematically illustrate a cross-sectional view and a plan view of an apparatus according to the present disclosure.

The Figures are not necessarily to scale. Certain features and views of the figures may be shown schematically or exaggerated in scale in the interest of clarity and conciseness. For example, the dimensions of some elements in the figures may be exaggerated relative to other elements to aid explication. Similar reference numerals are used in the Figures to designate similar features. For clarity, all reference numerals are not necessarily displayed in all figures.

DETAILED DESCRIPTION

Figure 1B:
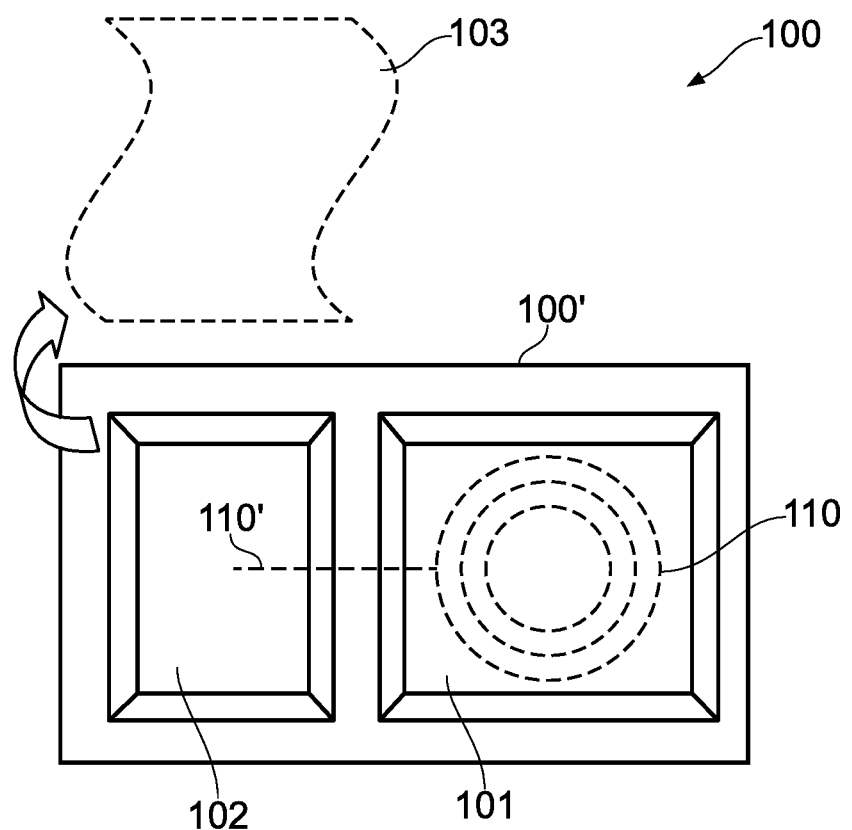

FIG. 1A schematically illustrates a cross sectional view of an apparatus 100 for storing and dispensing dental floss 110, and FIG. 1B schematically illustrates a plan view of the apparatus.

The apparatus 100 comprises a first compartment 101 integrally formed with a second compartment 102. The first compartment is configured, in use, to house dental floss. The second compartment is configured, in use, to provide the user access to a length 110' of stored dental floss for dispensement there from. The second compartment is closed by a sealing member 103. At least a portion of the sealing member is configured to be detachable to provide user access to the interior of the second compartment so as to provide, in use, user access to the length of the stored dental floss for dispensement, i.e. such that a user can manually grasp an end portion of the dental floss that is present in the second compartment to pull out/extract a desired length of floss to be severed and used.

The first and second compartments may be integrally formed as a single piece/unitary structure formed from a continuous body member 100'. The integrally formed first and second compartments may be manufactured via any suitable means, for example vacuum-formed or injection moulded. The first and second compartments may form cavities/pockets in a formable web. For example, first and second cavities/pockets may be formed from a roll or sheet of plastic material, such as a thermosetting plastic, upon application of heat and pressure via a dye.

The first compartment housing the dental floss may be configured so as to store/receive dental floss, not least for example in the form of a roll or bobbin of dental floss that is rotatably stored within the first compartment.

The sealing member closes at least the second compartment so as to form a closure/lid for at least the second compartment. In some examples, the second compartment is of the form of an open-ended container, comprising side walls and a base, which is closed on its upper surface by the sealing member. The sealing member may take the form of one or more of: a sheet, a film, a foil, a laminate or a sheet of material. At least a portion of the sealing member is configured to be detachable, i.e. so as to be user removably attached. This may be affected by one or more of: one or more weakened or perforated sections that enable a user to remove a portion of the sealing member. The detachability of the sealing member could also be affected via any other suitable means, not least for example via the use of an adhesive of a suitably weak adhesive strength or a weld/seam of a relatively low strength that are appropriately configured to maintain the sealing means in attachment with the second compartment, yet still enable a user to readily manually detach the sealing member, e.g. such that at least portion of the sealing member may be able to be peeled off from the second compartment thereby providing the user to access the interior of the second compartment. In use, an end 110' of the length of the stored dental floss 110 is provided in the second compartment, such that, once the sealing member has been detached, a user is able to access the interior of the second compartment and thus is able to access the end of the dental floss 110' to pull out/extract a desired length of the same for dispensement from the apparatus.

In some examples, the sealing member seals the second compartment so as to provide an airtight seal for the compartment and/or a substantially hermetic seal. This may enable a preservation of the freshness of the stored dental floss (which may comprise volatile chemical that would otherwise evaporate and escape).

The term "dental floss" may be interchangeably referred to as dental tape or dental cord.

In some examples, the sealing member comprises a sheet of flexible material. However, in other examples, the sheet may be of a rigid material, such as card or rigid plastic material.

The first compartment may itself also be closed by a sealing member. In some examples, the sealing member of the first compartment comprises a part of the same sealing member used to close the second compartment, i.e. the same sheet/substrate may be used to close both the first and second compartments. However, whilst the portion of the sealing member closing the second compartment is configured to be user detachable, the portion of the sealing member configured to close the first compartment may be configured to be securely attached to the first compartment, i.e. so as to prevent user detachment there from and to prevent user access to the first compartment. This may be achieved by any appropriate means, not least for example the use of a strong adhesive, or a more robust weld/seam than that used to join the portion of the sealing member closing the second compartment.

The sealing member of the second compartment may be independently and separately detachable, i.e. such that the sealing member of the first compartment remains securely attached even after the sealing member of the second compartment has been detached.

The secure attachment of the sealing member to the first compartment may enable the dental floss stored therein to be kept sealed within the first compartment so as to maintain its freshness (the dental floss may comprise volatile chemicals which could otherwise escape and fade over time if the compartment were not adequately sealed).

Accordingly, in various examples of the invention, even though the same integral/unitary sealing member may be used to cover/enclose both the first and second compartments so as to form a closure/lid for each of the two compartments, the first compartment is able to be kept securely sealed even after the sealing member of the second compartment has been detached (for opening/exposing the second compartment to enable user access to manually grasp an end section of the dental floss which is provided in the second compartment) whilst the rest/majority of the dental floss remains sealed within the first compartment.

Figure 2:
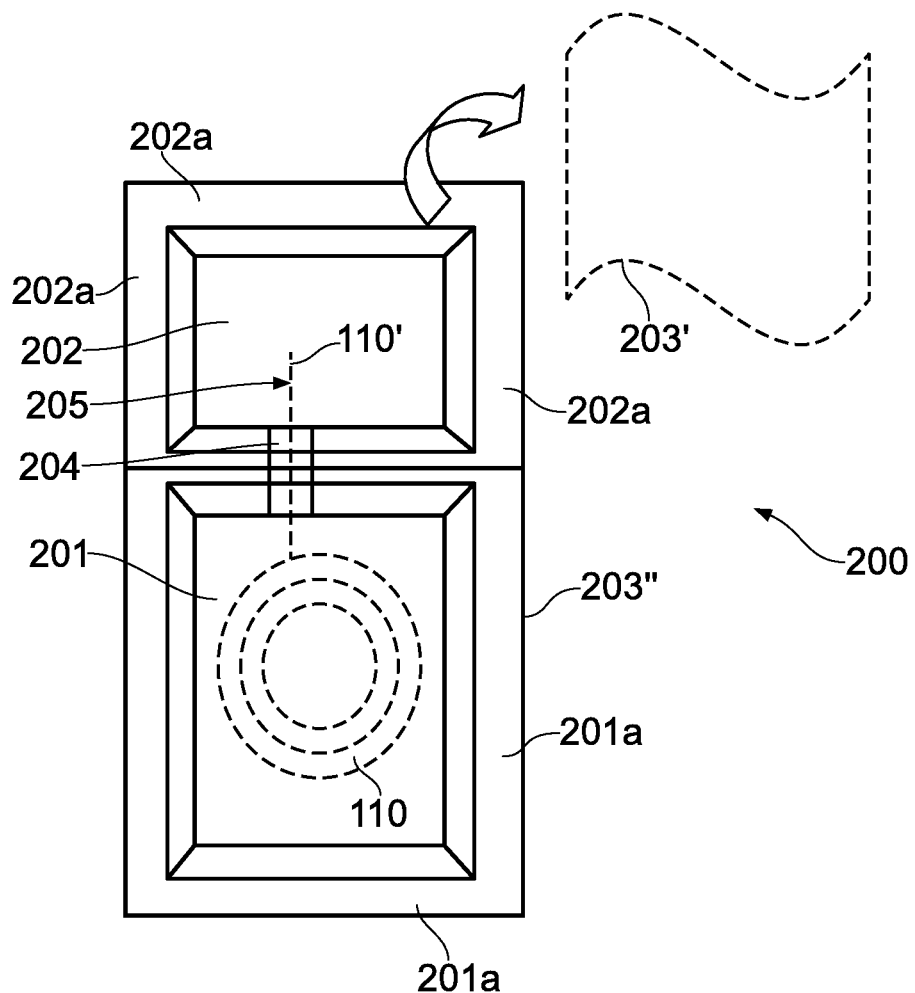
FIG. 2 schematically illustrates a further apparatus according to the present disclosure.

FIG. 2 shows a further example of an apparatus 200 according to the present disclosure wherein a transit section 204 is provided between the first compartment 201 and the second compartment 202 that enables a length 110' of the dental floss 110 to transit and pass between the first compartment 201 to the second compartment 202 via the transit section 204. The first compartment 202 has peripheral flange/rim sections 202a via which a portion of the sealing member 203' is securely attachably affixed. FIG. 2a shows a portion of the sealing member 203' having been removed from the second compartment, i.e. a user having peeled the sealing section 203' from the second compartment so as to reveal and expose the interior of the second compartment such that the user may have access to an end 110' of the length of dental floss that is provided in the second compartment such that a user can pull out a desired length of dental floss and cut it via the cutting means 205 so as to thereby effect dispensement of the dental floss from the second compartment 202. The first compartment 201 comprises peripheral flange/rim portions 201a via which a further portion of the sealing member 203" is securely attached, i.e. attached in the manner such that it is not readily user removable. Thus, whilst a second portion of the sealing member 203' is designed and configured so as to be user removed (and indeed in some examples it is configured to be re-attachable/re-sealable to the second compartment) the first portion of the sealing member 203" is designed to be securely fixed to the first compartment to provide a superior seal so as to preserve the freshness of the dental floss stored therein. In FIG. 2, the further portion of the sealing member 203" is transparent, though in other examples it could be opaque or partially transparent.

The cutting means may comprise any suitable means for cutting or severing a length of dental floss, not least for example a blade, cutting fitment or other device/mechanism for enabling the cutting of the dental floss for dispensement form the second compartment. The cutting blade/element may be of any suitable material, such as a metal or plastic, duly configured and sharpened to provide a cutting surface.

Figure 3:
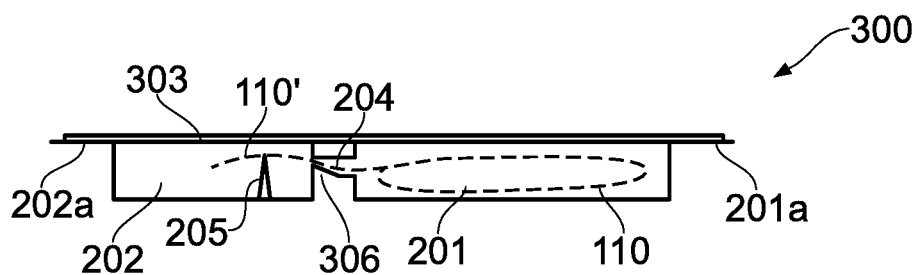
FIG. 3 schematically illustrates a yet further apparatus according to the present disclosure.

FIG. 3 shows a cross-sectional view of an apparatus 300, similar to the apparatus 200 of FIG. 2. The apparatus additionally comprises a tensioning means 306 that may be provided as part of the transit section/passageway between the first compartment 201 and the second compartment 202. The tensioning means is configured to impart a resistance to the movement of dental floss stored in the first compartment 202 through the passageway and into the second compartment 202. Thus, when a user pulls an end length of the dental floss 110' from the second compartment, a tension is applied to the length of dental floss which may facilitate the drawing of the section of the dental floss across an edge of the blade thereby facilitating the cutting of the length of the dental floss on the cutting means 204. The tensioning means for resisting/impeding the excess of the dental floss from the first compartment to the second compartment may be provided by any suitable means that provides resistance to the movement of the dental floss, for example via the provision of passageway whose dimensions are configured to constrict the ready movement of the dental floss there along, for example one or more narrowing of the passage of the passageway or a convoluted meandering passageway between the first and second section.

In various examples of the present disclosure, the apparatus may be formed as a blister pack wherein the compartments are manufactured by thermoforming a sheet of plastic so as to define the first and second compartments as "blisters"/pockets of the thermoformed plastic. Once the dental floss has been placed in the first compartment and an end section of the dental floss has been provided through the transiting section and tensioning means so as to provide an end length of the dental floss in the second compartment, the two compartments are then closed/sealed. Such closure/sealing may be via the sealing member being affixed to the compartments, for example via adhesive or welding, but in a manner so as to ensure that the sealing member covering the second compartment is user detachable/removable so as to enable user access to the interior of the second compartment, i.e. so as to enable a user to pull the end of the dental floss and dispense the dental floss by cutting the end section to a desired length.

Figure 4:
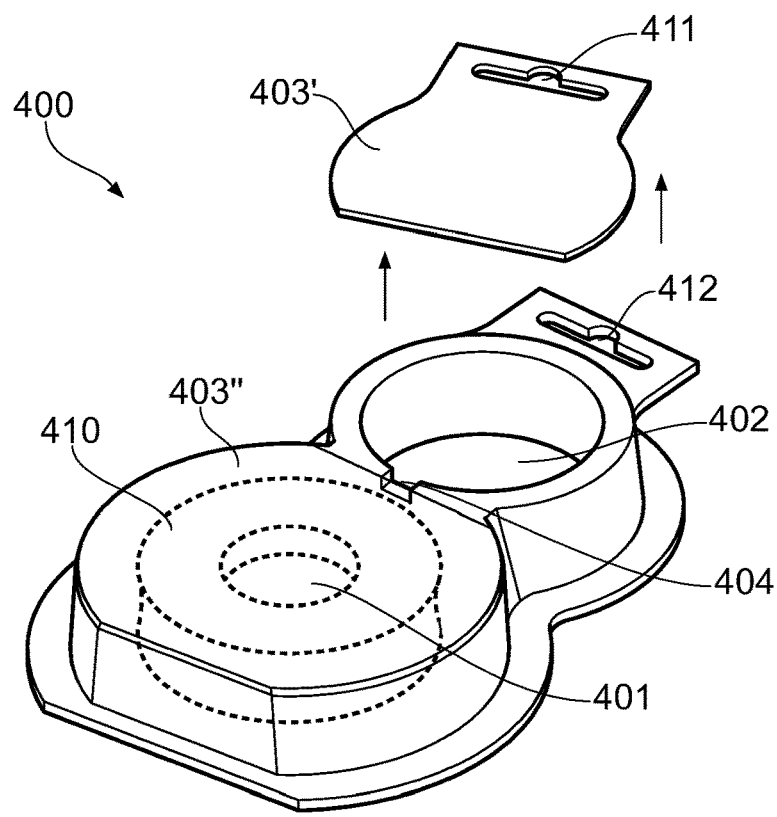
FIG. 4 schematically illustrates a yet further apparatus according to the present disclosure.

FIG. 4 illustrates an apparatus 400 comprising a first compartment 401 for housing a bobbin of dental floss 410 and a second compartment 402 integrally formed with the first compartment 401. A transition section 404 is provided between the first and second compartments for enabling an end length of the dental floss 410 to pass from the first compartment to the second compartment for user access there from for dispensement, i.e. once a second portion of the sealing member 403' has been detached to allow user access to the interior of the second compartment 402. FIG. 4 shows the apparatus with the second part of the sealing member 403' having been removed whilst the first part of the sealing member 403" forming a closure for the first compartment 401 remaining firmly fixed to the first compartment securely sealing the dental floss 410 therein. A portion of the sealing member 403' may be provided with an aperture 411 or orifice for enabling the apparatus to be hung on a retail display hook or a eurohook in a retail environment. A main body portion of the apparatus, such as a flange portion extending from the second compartment 402 may also be provided with a similar aperture 412 for enabling the apparatus to be hung in a retail environment.

Certain examples of the present disclosure provide a combined retail package and container into one device/product, thereby providing a simplified device/product that also reduces the amount of materials required to manufacture the same, i.e. as compared to providing separate dental floss container and retail packaging for the same.

The apparatus may enable a saving of materials, i.e. the use of less plastic, and providing both a combined retail display package as well as dental floss container/dispenser product. Moreover, examples of the apparatus may enable the stored dental floss product to be kept fresh via an all-encompassing plastic pack that can be substantially hermetically sealed.

Between the two compartment blisters, there is a transit section which also may provide a tension to the stored dental floss when being pulled by a user for dispensement from the second compartment 402.

The apparatus 400 takes the form of a blister pack comprising two compartments, the first compartment 401 designed to house a bobbin of dental floss. A cutting fitment is provided in the second compartment 402. A foil or plastic closure/film is provided to close the first and second compartments. The closure for the second compartment is configured so as to be user detachable i.e. so as to enable a user to peel back the part of the foil or plastic film to expose an end portion of the dental floss and cutting fitment of the second compartment whilst the dental floss bobbin remains contained within the sealed first compartment.

The apparatus 400 provides not only a retail package for dental floss, but also provides a container for housing and dispensing dental floss. The apparatus comprises a cutter as well as a transit section between the first and second compartments such that as the floss is pulled out by a user via the second compartment, sufficient resistance is provided to the floss to allow it to be drawn across the cutter so as to facilitate the severing of the end length of the dental floss from the remainder of the stored dental floss.

The main body of the apparatus, i.e. in which the first and second compartments are integrally formed, may be made from injection moulded plastic or it could be made via a vacuum formed blister materials or a clam shell blister. The second compartment is sealed in a manner that enables the opening of the seal via a sealing film, foil or even a resealable lid. Such compartments and the sealing of the same may be readily formed and produced via a simple mass-production manufacturing process such that the manufacture of the apparatus may be simply effected at a low cost.

The first compartment may be formed so as to additionally comprise a container whose shape broadly corresponds to that of the dental floss container, for example a cylindrical shaped open-ended container for receiving a bobbin or roll of dental floss. The first compartment may additionally comprise a means for acting as an axle for such a bobbin or roll of dental floss that which the bobbin or roll may rotate when a user is pulling/drawing out an end section of the dental floss from the second compartment via the transit section.

The second member of the sealing member that seals and closes the second compartment is configured to be detachable/removable independently from the first section of the sealing member sealing/closing the first compartment, i.e. such that the second section of the sealing member may be detached/removed by a user from the second compartment to expose the interior for providing user access thereto, whilst the first sealing member continues to seal/close the first compartment.

Figure 5:
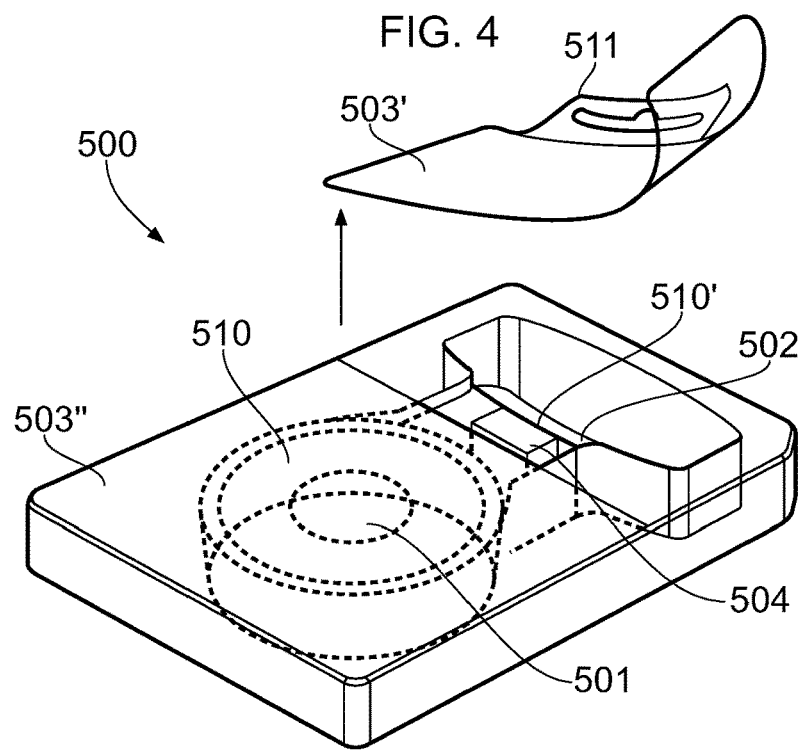
FIG. 5 schematically illustrates a yet further example of an apparatus according to the present disclosure.

FIG. 5 shows a yet further apparatus 500 comprising a first compartment 501 for housing a bobbin of dental floss 510, an end portion of the dental floss 510' is provided via a transition section 504 which imparts a tension to the dental floss when pulled by a user to extract a length thereof for cutting and dispensement from the second compartment 502. The first compartment 501 is sealed and closed by a first sealing member 503" whilst the second compartment 502 is sealed and closed by a second portion of a sealing member 503' which is readily detachable by a user to enable user access to the interior of the second compartment 502 and in particular access to the end length 510' of the dental floss to pull out a desired length and cut the length via a cutting lever that may be additionally comprised in the transition section 504 to enable dispensement of the dental floss. In the apparatus of FIG. 500, an aperture 511 for enabling the apparatus to be hung by a retail hook such as a eurohook is provided only on the sealing member 503' (and no such aperture is provided on the main body that provides the integrally formed first and second compartments). The apparatus 500 is configured to be self-standing having a substantially flat lower/base surface 513 that is dimensioned (e.g. has a width/depth) sufficient to enable the apparatus to stand upright and be self-supported on the lower/base surface 513.

Figure 6:
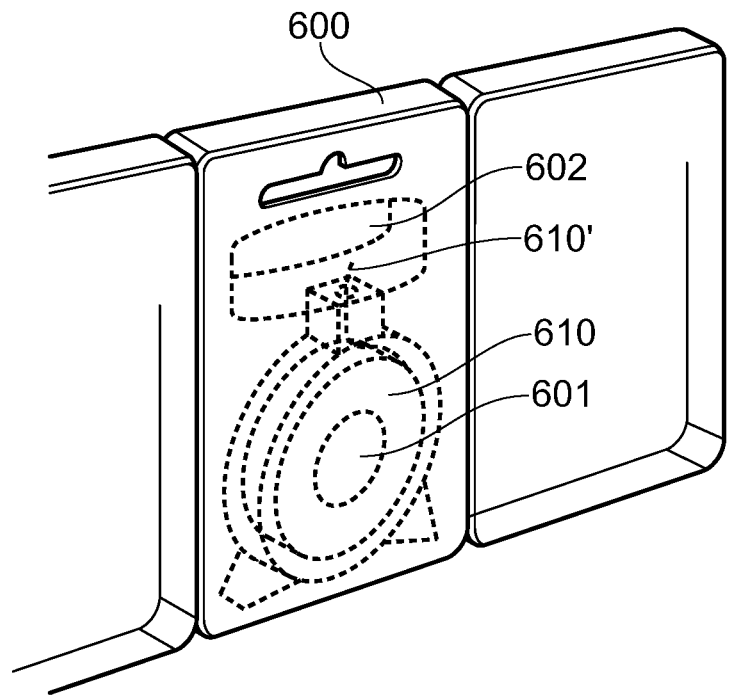
FIG. 6 schematically illustrates a yet further example of an apparatus according to the present disclosure.

FIG. 6 illustrates a yet further apparatus 600 having first and second compartments 601 and 602 for storing dental floss 610 in the first compartment and enabling user access to an end length of the dental floss 610' from the second compartment 602. The apparatus is configured to be self-supporting such that it can be readily stacked on shelves in a retail environment and stored upright in a domestic environment.

Figure 7:
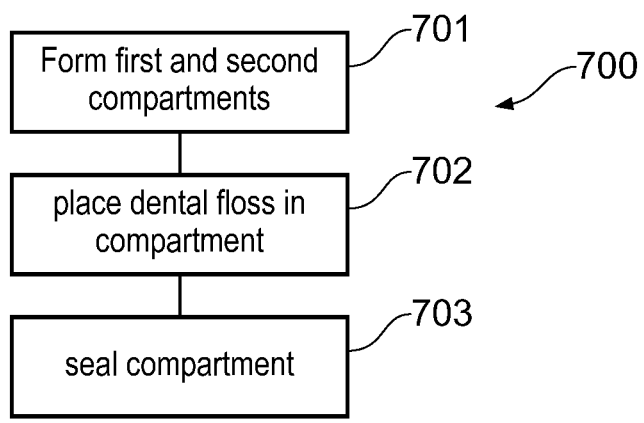
FIG. 7 schematically illustrates a method according to the present disclosure.

FIG. 7 schematically illustrates a method 700 for manufacturing an apparatus for storing and dispensing dental floss.

In block 701, the first and second compartments are integrally formed in a body member. The first compartment is configured such that, in use, it can store dental floss whilst the second compartment is configured, in use, to provide user access to a length of the stored dental floss provided therein. Once the compartments have been formed, dental floss is placed in the first compartment in block 702. An end section of the dental floss stored in the first compartment is provided in the second compartment. In block 703, the second compartment is sealed with a sealing member, such that at least a portion of the sealing member is detachable to provide user access to the interior of the second compartment (and the end section of the dental floss provided therein). The provision of such a sealing member being detachable may correspond to the sealing member being attached to the second compartment via a structural weakness, such as a weakened section/perforation of the sealing member, the sealing member and/or an adhesive for the same being of sufficient weakness to enable a user to readily detach the sealing member from the second compartment. Such user detachability may comprise a user detaching the sealing member from the second compartment manually himself/herself without requiring additional tools, such as scissors. The first compartment itself may be sealed with a sealing member. Such a sealing member for the first compartment may correspond to that used for the second compartment, i.e. such that a single unitary sheet of material is used for a sealing member for both the compartments. The sealing member for the first compartment is securely attached to the first compartment (as compared to the sealing member for the second compartment being user detachable or even re-attachable to the second compartment).

Features described in the preceding description may be used in combinations other than the combinations explicitly described. Although functions have been described with reference to certain features, those functions may be performable by other features whether described or not. Although features have been described with reference to certain examples, those features may also be present in other examples whether described or not. Although various examples of the present disclosure have been described in the preceding paragraphs, it should be appreciated that modifications to the examples given can be made without departing from the scope of the invention as set out in the claims.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some or all other examples. Thus 'example', 'for example' or 'may' refers to a particular instance in a class of examples. A property of the instance can be a property of only that instance or a property of the class or a property of a sub-class of the class that includes some but not all of the instances in the class.

In this description, references to "a/an/the" [feature, element, component, means . . . ] are to be interpreted as "at least one" [feature, element, component, means . . . ] unless explicitly stated otherwise.

The above description describes some examples of the present disclosure however those of ordinary skill in the art will be aware of possible alternative structures and method features which offer equivalent functionality to the specific examples of such structures and features described herein above and which for the sake of brevity and clarity have been omitted from the above description. Nonetheless, the above description should be read as implicitly including reference to such alternative structures and method features which provide equivalent functionality unless such alternative structures or method features are explicitly excluded in the above description of the examples of the present disclosure.

Whilst endeavoring in the foregoing specification to draw attention to those features of examples of the present disclosure believed to be of particular importance it should be understood that the applicant claims protection in respect of any patentable feature or combination of features hereinbefore referred to and/or shown in the drawings whether or not particular emphasis has been placed thereon.

The examples of the present disclosure and the accompanying claims may be suitably combined in any manner apparent to one of ordinary skill in the art.

What is claimed:

1. An apparatus for housing and dispensing dental floss, the apparatus comprising:
　a body member configured to define a first compartment integrally formed with a second compartment, the second compartment comprising side walls and a base;
　a sealing member configured to close the first and second compartments; and
　a cutting device configured to cut dental floss;
　wherein the first compartment is configured, in use, to house dental floss;
　wherein the second compartment is configured, in use, to provide user access to a length of the housed dental floss for dispensement therefrom;
　wherein a first portion of the sealing member is configured to close the first compartment,
　wherein a second portion of the sealing member is configured to close the second compartment; and
　wherein the second portion of the sealing member is configured to be detachable to provide user access to the interior of the second compartment so as to provide, in use, access to the length of the stored dental floss for dispensement; and
　wherein the second portion of the sealing member is configured to be detachable independently of the first portion of the sealing member such that the first portion of the sealing member can remain attached whilst the second portion of the sealing member is detached.

2. The apparatus of claim 1, wherein the sealing member comprises a flexible sheet of material.

3. The apparatus of claim 1, wherein the second portion of the sealing member is configured to be re-attachable to the second compartment.

4. The apparatus of claim 1, wherein the first portion of the sealing member is configured to be securely attached to the first compartment.

5. The apparatus of claim 1, further comprising a passageway between the first compartment and the second compartment, wherein the passageway is configured to enable, in use, the passage of one or more lengths of dental floss stored in the first compartment to be accessed and dispensed from the second compartment.

6. The apparatus of claim 1, wherein the second portion of the sealing member extends from the first portion of the sealing member.

7. The apparatus of claim 1, further comprising a mechanism configured to impart resistance to movement of the dental floss.

8. The apparatus of claim 1, wherein the apparatus is formed as a blister pack.

9. The apparatus of claim 1, wherein the sealing member comprises an aperture configured to use with one of more of: a retail display hook, and a euro hook.

10. The apparatus of claim 1, wherein the apparatus is configured to be self-standing.

11. The apparatus of claim 1, wherein the apparatus further comprises the dental floss.

12. A combined retail package and dispenser for dental floss comprising the apparatus of claim 1.

13. The apparatus of claim 1, wherein the sealing member is integrally formed with the first and second compartments.

14. The apparatus claim 1, wherein the apparatus is configured to form a clam shell blister pack.

15. A method for manufacturing an apparatus for storing and dispensing dental floss, wherein the apparatus comprises a cutting device configured to cut dental floss, the method comprising:
　integrally forming first and second compartments in a body member, the second compartment comprising side walls and a base, wherein the first compartment is configured, in use, to store dental floss, and wherein the second compartment is configured, in use, to provide user access to a length of the stored dental floss;
　placing dental floss in the first compartment;
　sealing the first and second compartments with a sealing member such that a first portion of the sealing member closes the first compartment and a second portion of the sealing member closes the second compartment, and wherein the second portion of the sealing member is detachable to provide user access to the interior of the second compartment and
　wherein the second portion of the sealing member is configured to be detachable independently of the first portion of the sealing member such that the first portion of the sealing member can remain attached whilst the second portion of the sealing member is detached.

16. The method of claim 15, further comprising:
　securely attaching the first portion of the sealing member to the first compartment.

17. The method of claim 15, wherein the second compartment is sealed with the second portion of the sealing member such that the portion of the sealing member is re-attachable.

18. The method of claim 15, further comprising:
　sealing the first and second compartments with a unitary sealing member.

* * * * *